US010495625B2

(12) United States Patent
Heo

(10) Patent No.: US 10,495,625 B2
(45) Date of Patent: Dec. 3, 2019

(54) SYSTEM FOR PREDICTING RESIDUAL SERVICE LIFE OF FIRE-DAMAGED CONCRETE STRUCTURES AND METHOD FOR THE SAME

(71) Applicant: KOREA INSTITUTE OF CIVIL ENGINEERING AND BUILDING TECHNOLOGY, Gyeonggido (KR)

(72) Inventor: Young Sun Heo, Gyeonggi-do (KR)

(73) Assignee: KOREA INSTITUTE OF CIVIL ENGINEERING AND BUILDING TECHNOLOGY, Gyeonggido (KR)

( * ) Notice: Subject to any disclaimer, the term of this patent is extended or adjusted under 35 U.S.C. 154(b) by 299 days.

(21) Appl. No.: 15/537,435

(22) PCT Filed: Oct. 28, 2015

(86) PCT No.: PCT/KR2015/011402
§ 371 (c)(1),
(2) Date: Jun. 19, 2017

(87) PCT Pub. No.: WO2016/099027
PCT Pub. Date: Jun. 23, 2016

(65) Prior Publication Data
US 2017/0350872 A1    Dec. 7, 2017

(30) Foreign Application Priority Data
Dec. 19, 2014    (KR) .................. 10-2014-0184431

(51) Int. Cl.
G01N 33/38    (2006.01)
G06F 17/30    (2006.01)
(Continued)

(52) U.S. Cl.
CPC ...... *G01N 33/383* (2013.01); *G06F 16/24528* (2019.01); *G06Q 50/08* (2013.01); *B28B 11/245* (2013.01)

(58) Field of Classification Search
CPC .. G01N 33/383; C04B 28/04; C04B 40/0231; G06Q 10/06; G06N 20/00; B28B 11/245
(Continued)

(56) References Cited

U.S. PATENT DOCUMENTS 6,860,932 B2 *   3/2005   Oshida .................. A61K 6/033
                                                        106/35
6,959,270 B2 *  10/2005   Marchand ............ G01N 33/383
                                                        106/640
(Continued)

FOREIGN PATENT DOCUMENTS

JP    2005-227065         8/2005
JP    2010032318 A  *    7/2008   ............. B28B 11/24
(Continued)

OTHER PUBLICATIONS

"International Search Report (Form PCT/ISA/210) of PCT/KR2015/011402", dated Feb. 29, 2016, with English translation thereof, pp. 1-4.

*Primary Examiner* — John E Breene
*Assistant Examiner* — Jeffrey P Aiello
(74) *Attorney, Agent, or Firm* — JCIPRNET

(57) ABSTRACT

Provided are: a system for predicting the residual lifespan of a fire-damaged concrete structure and a method therefor, the system being capable of acquiring sample data by performing a chemical analysis on a sample obtained from the fire-damaged concrete structure, comparing the obtained sample data with data pre-stored in a standardization DB so as to quickly predict the residual lifespan of the fire-damaged concrete structure, and accurately and scientifically assessing the level of fire damage of the fire-damaged
(Continued)

concrete structure so as to perform appropriate repair and reinforcement of the fire-damaged concrete structure.

10 Claims, 14 Drawing Sheets

(51) Int. Cl.
  *G06Q 50/08* (2012.01)
  *G06F 16/2452* (2019.01)
  *B28B 11/24* (2006.01)
(58) Field of Classification Search
  USPC .......................... 702/22, 34, 35, 181; 703/2
  See application file for complete search history.

(56) References Cited

U.S. PATENT DOCUMENTS

| | | | | |
|---|---|---|---|---|
| 9,388,072 B2* | 7/2016 | Niven | .................. | C04B 7/26 |
| 9,459,192 B2* | 10/2016 | Hosoda | ............... | G01N 33/383 |
| 9,638,652 B2* | 5/2017 | Ghods | ................. | G01N 27/026 |
| 9,679,244 B2* | 6/2017 | Ohno | ....................... | G06N 3/08 |
| 9,738,562 B2* | 8/2017 | Monkman | ........... | C04B 40/0231 |
| 9,790,131 B2* | 10/2017 | Lee | ......................... | C04B 22/10 |
| 2003/0040892 A1* | 2/2003 | Marchand | ............ | G01N 33/383 703/2 |
| 2013/0131999 A1 | 5/2013 | Hussain | | |
| 2014/0249788 A1 | 9/2014 | Marchand et al. | | |
| 2015/0193881 A1* | 7/2015 | Emison | .................. | G06Q 40/08 705/4 |
| 2016/0075603 A1* | 3/2016 | Neithalath | .............. | C04B 28/00 106/286.3 |

FOREIGN PATENT DOCUMENTS

| | | | | |
|---|---|---|---|---|
| JP | 2010-032318 | | 2/2010 | |
| JP | 2014006143 A | * | 6/2012 | ............... E04B 1/00 |
| JP | 2014-006143 | | 1/2014 | |
| KR | 20060017666 | | 2/2006 | |
| KR | 10-0631485 | | 9/2006 | |
| KR | 10-0835848 | | 6/2008 | |
| KR | 10-0894084 | | 4/2009 | |
| KR | 10-1128455 | | 3/2012 | |

* cited by examiner

[FIG. 1]
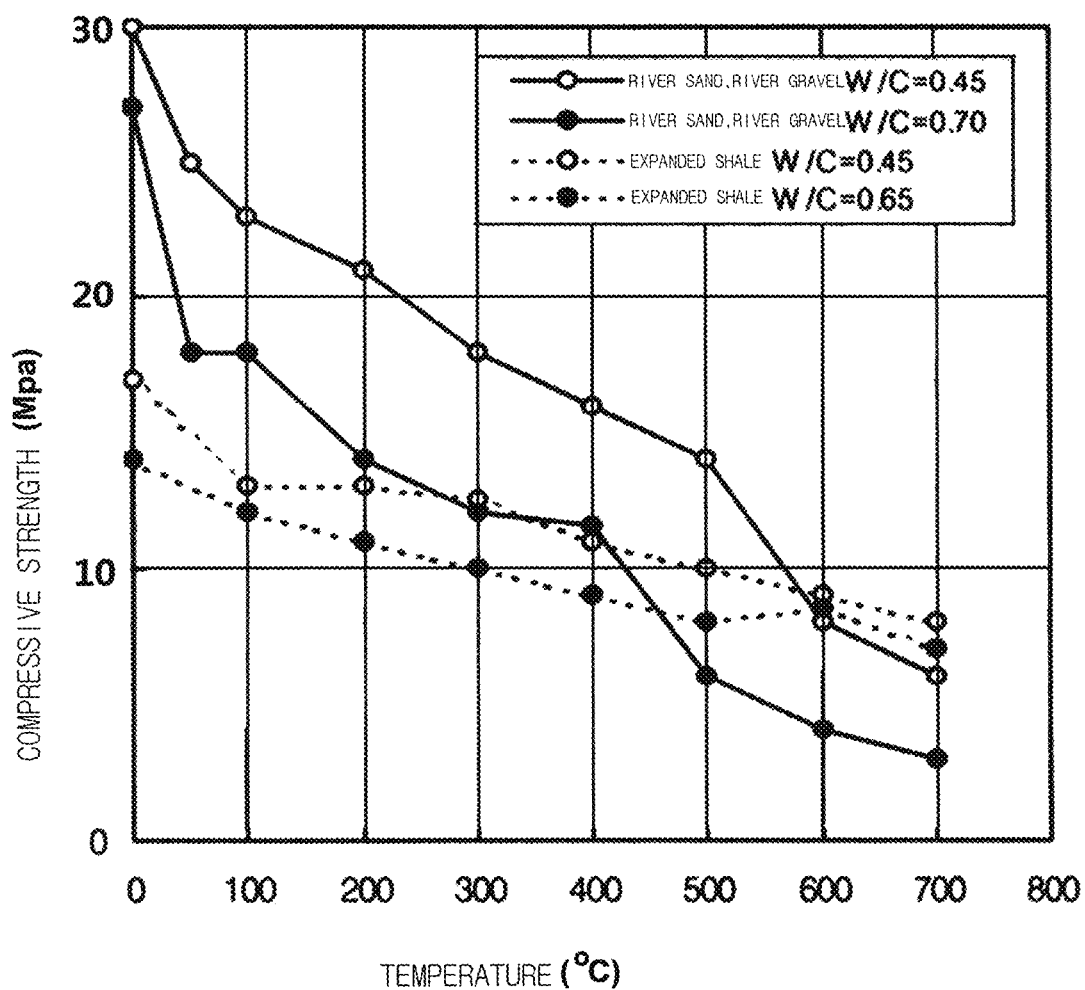

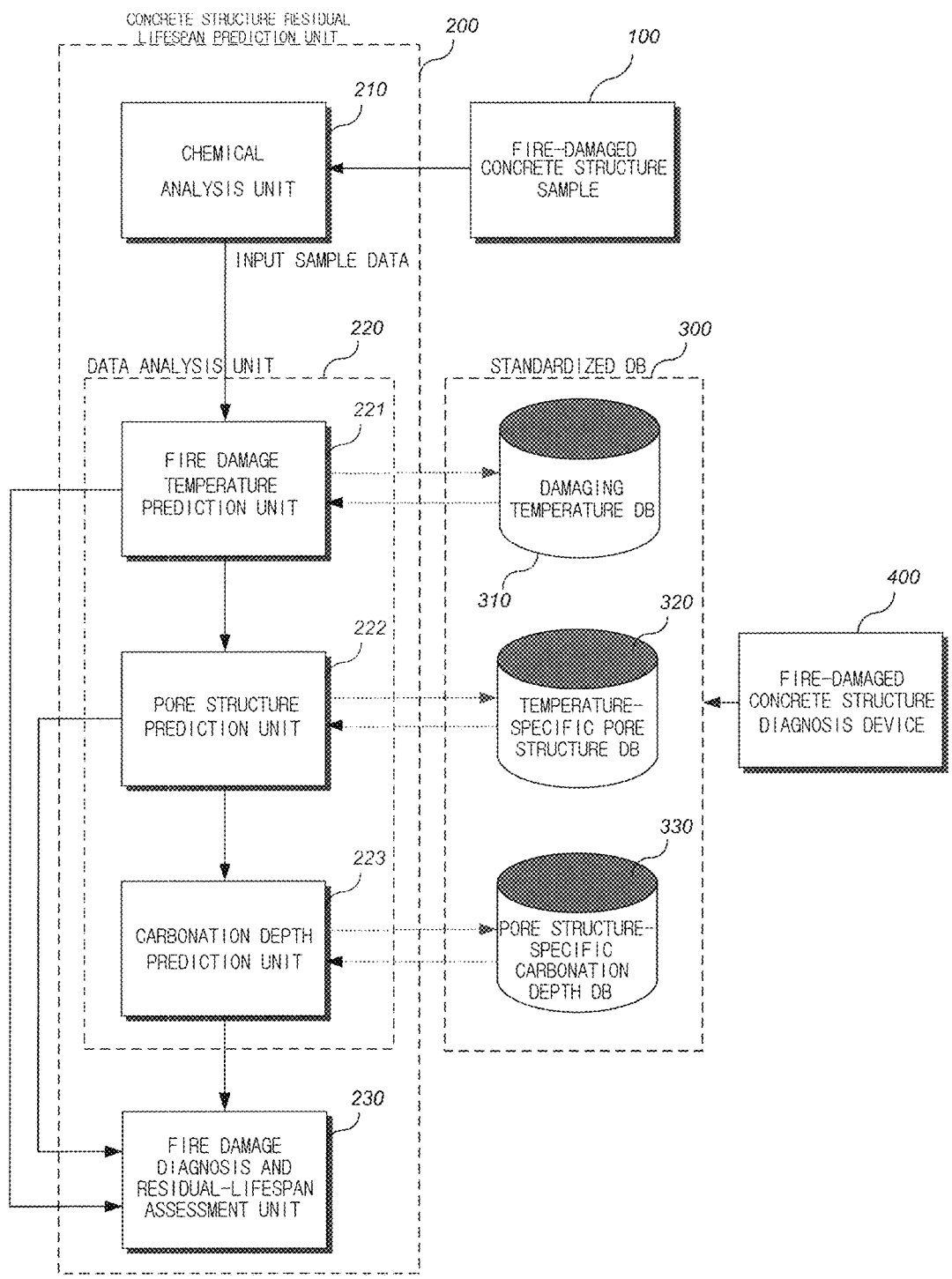
[FIG. 2]

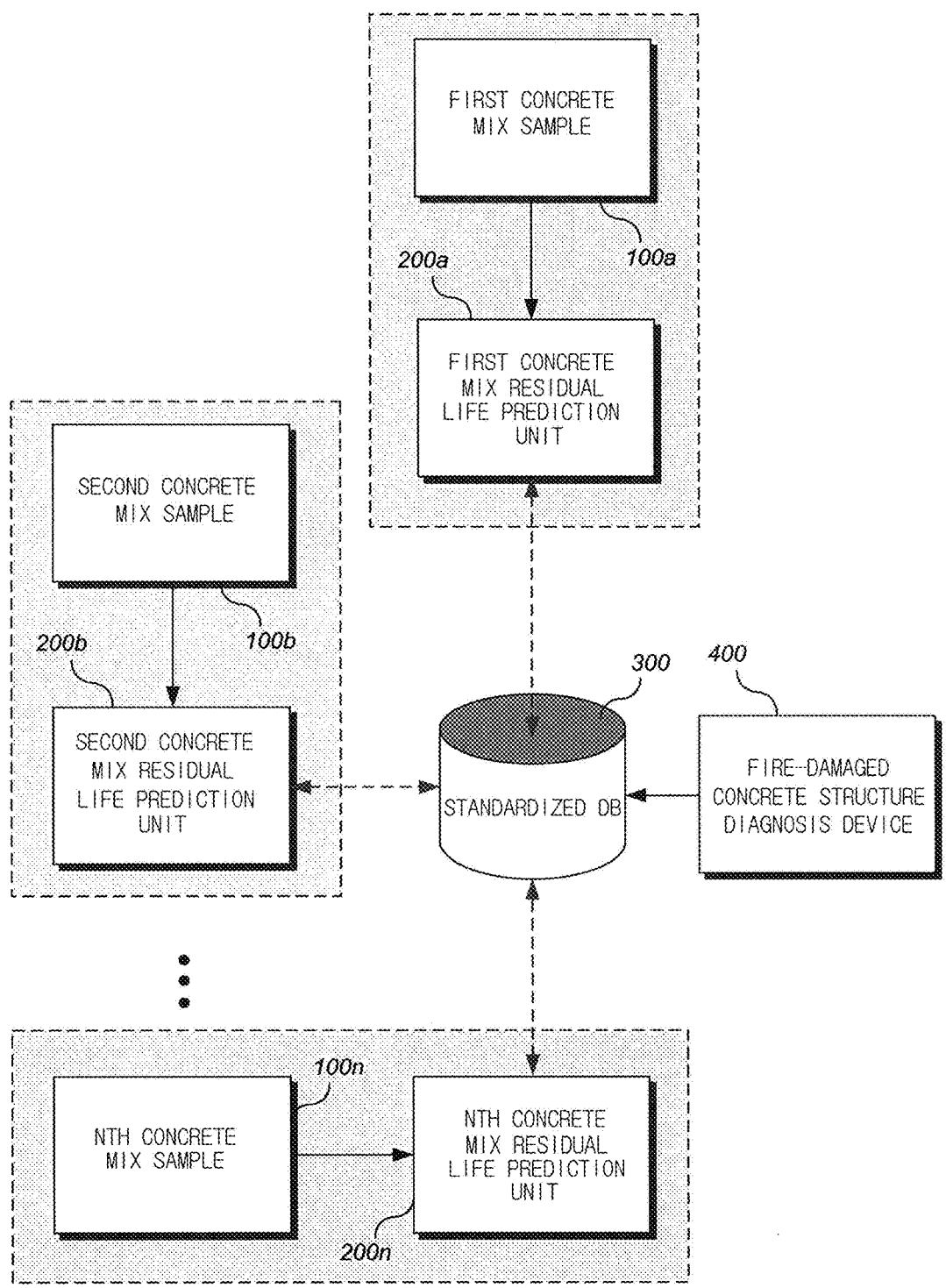
[FIG. 3]

[FIG. 4]
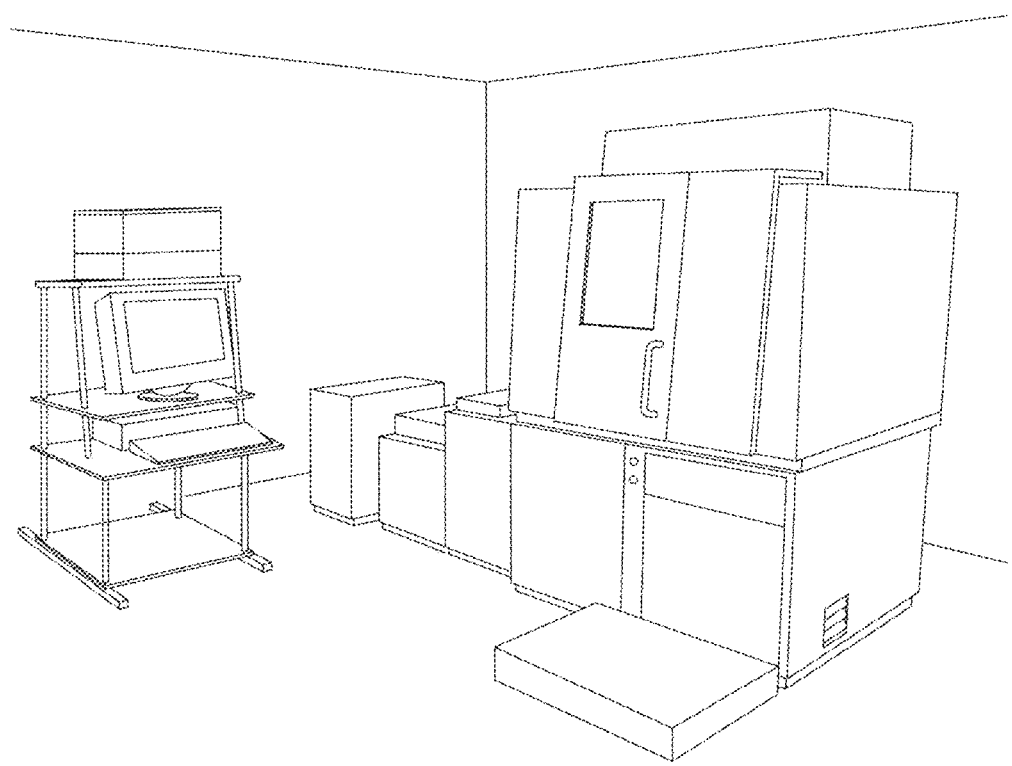

[FIG. 5A]
| | | |
|---|---|---|
| ● | SiO₂ | Silicon Oxide (Quartz) |
| ☆ | Ca(OH)₂ | Portlandite |
| ◇ | SiO₂ | Silicon Oxide (Feldspar) |
| × | CaCO₃ | Calcium Carbonate (Calcite) |
| + | CaO | Calcium Oxide |
[FIG. 5B]
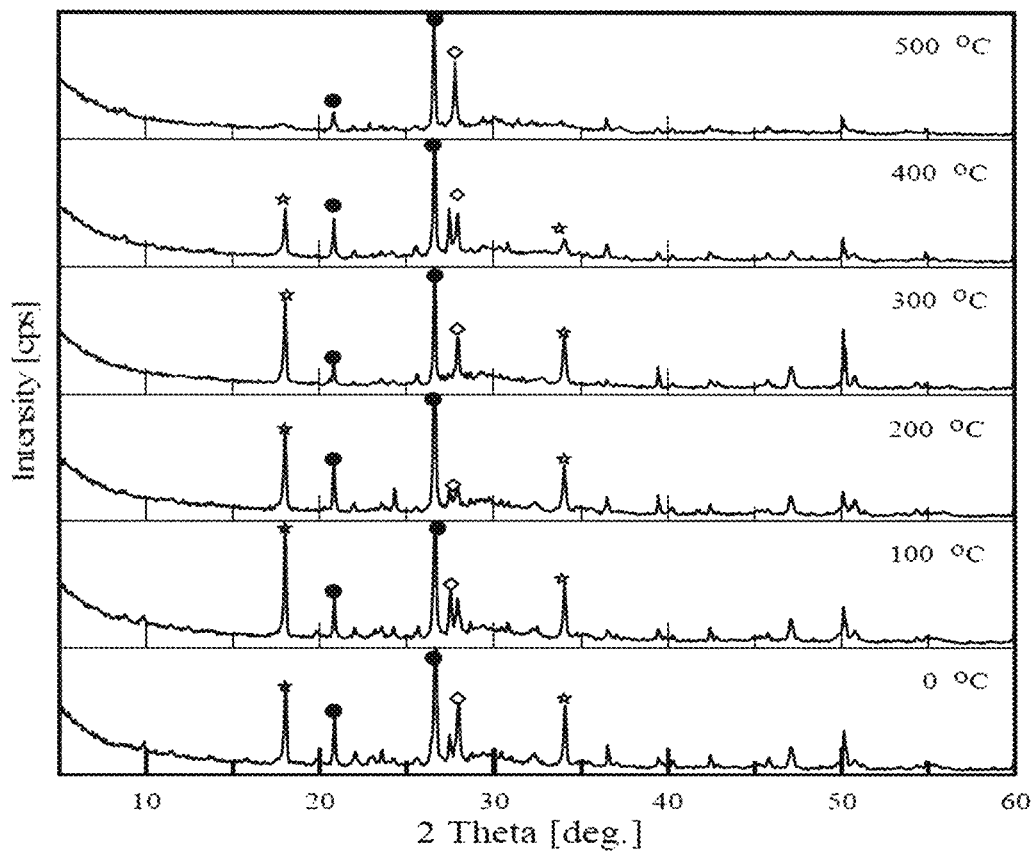

[FIG. 5C]
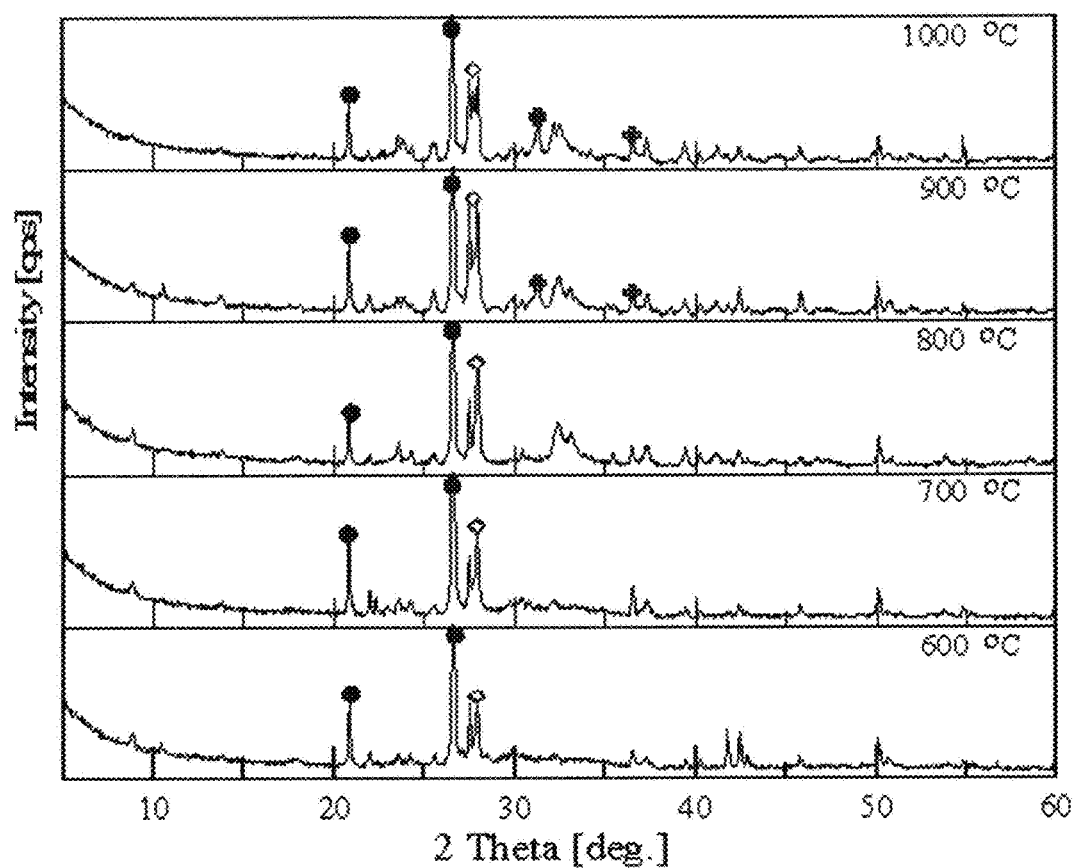

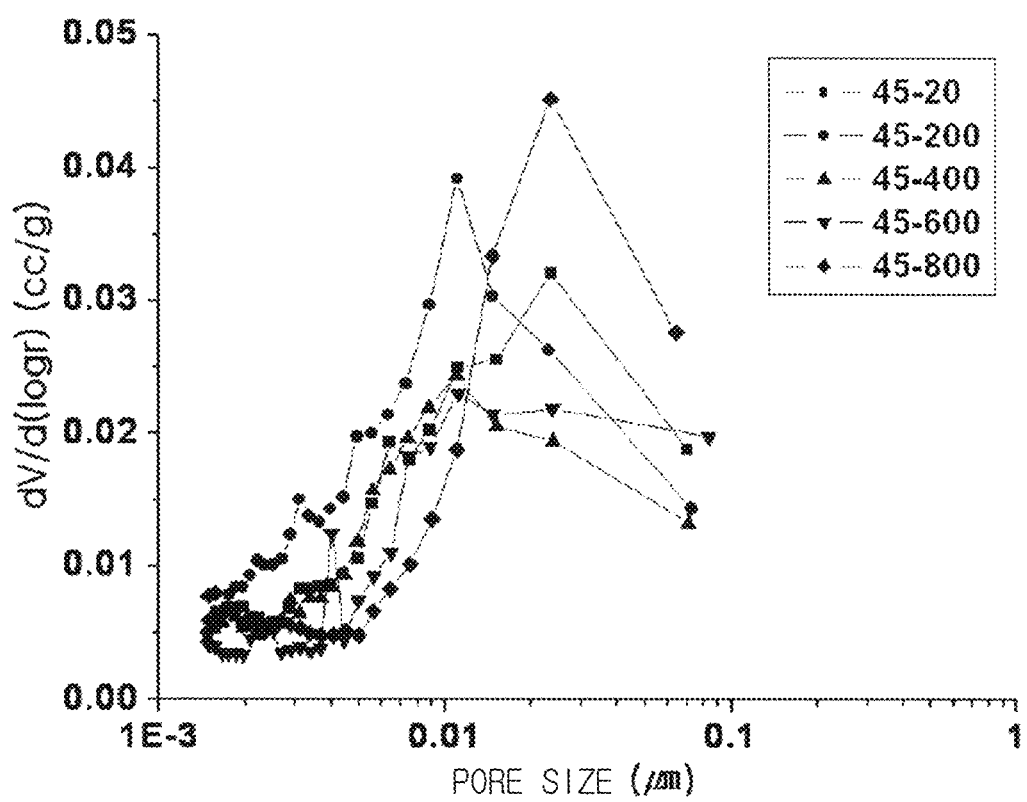
[FIG. 6A]

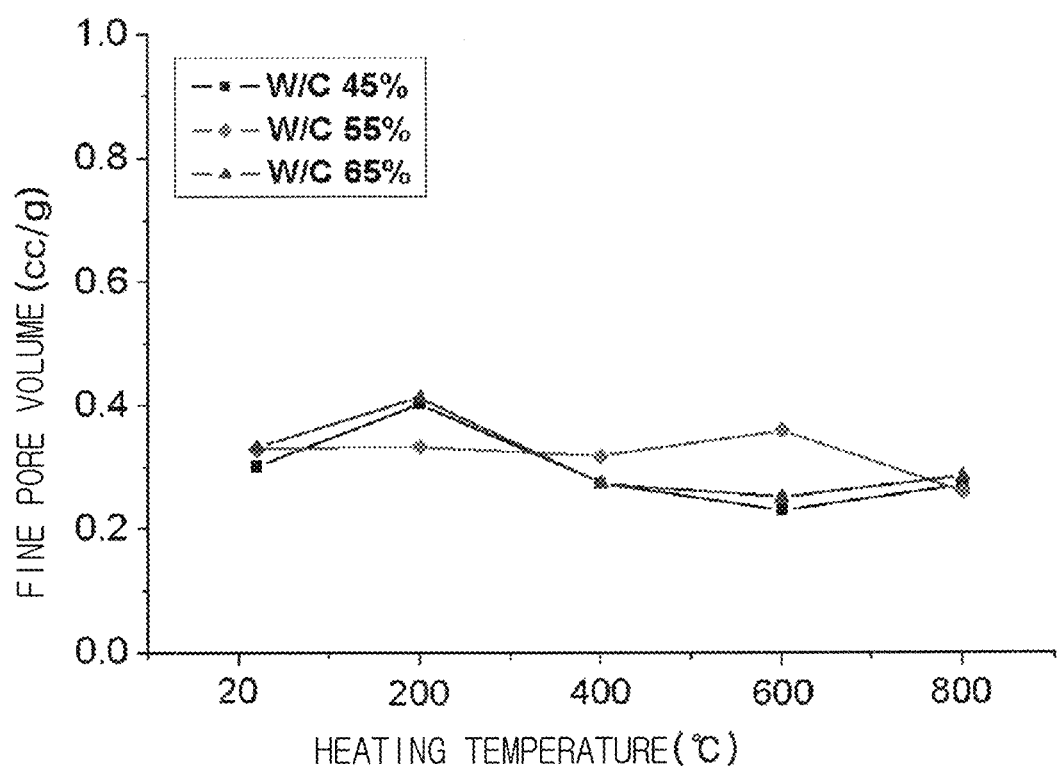
[FIG. 6B]

[FIG. 7A]
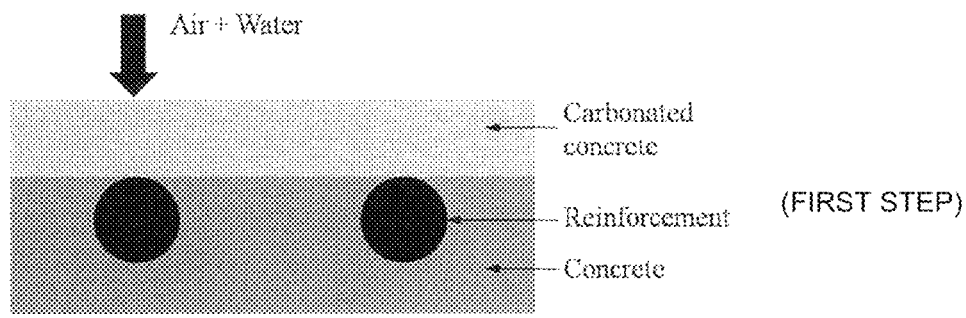
(FIRST STEP)
[FIG. 7B]
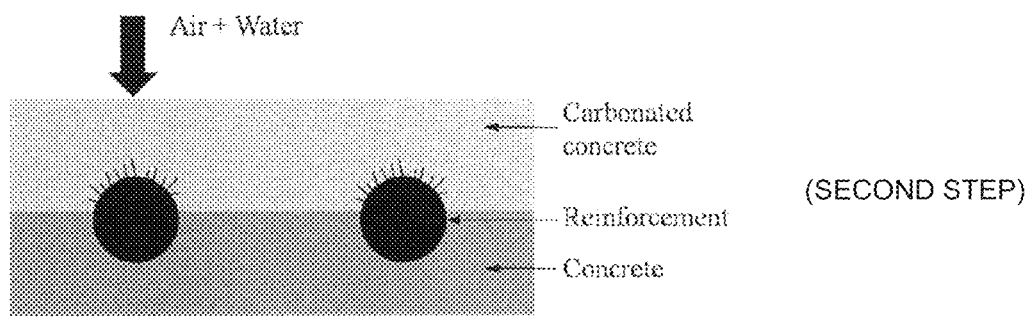
(SECOND STEP)
[FIG. 7C]
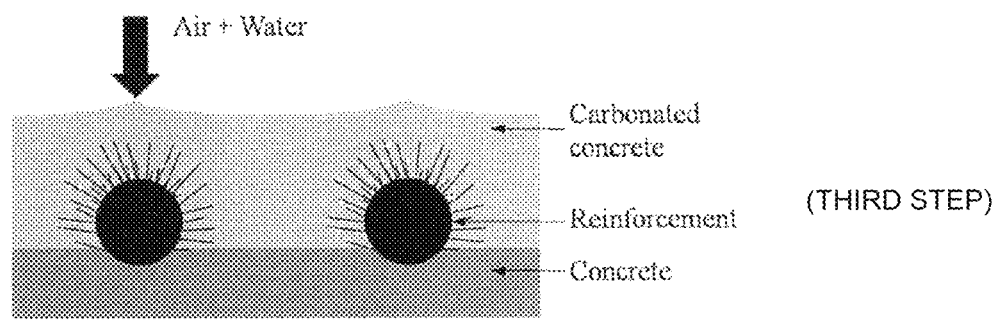
(THIRD STEP)

[FIG. 7D]
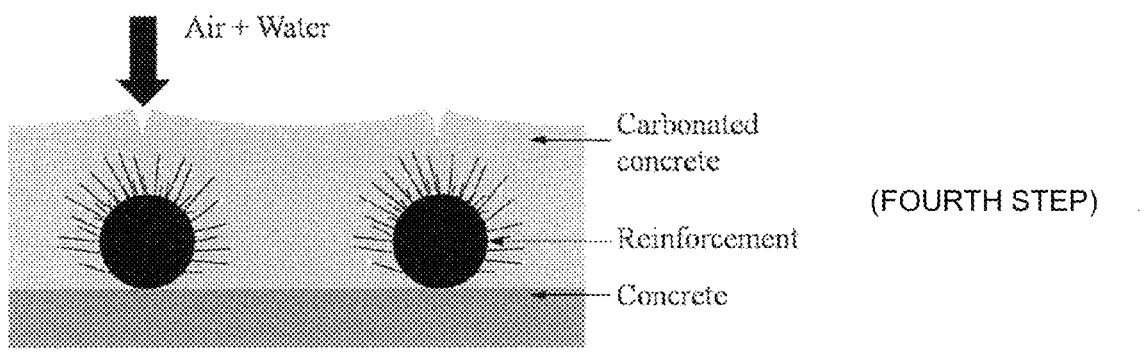
(FOURTH STEP)
[FIG. 7E]
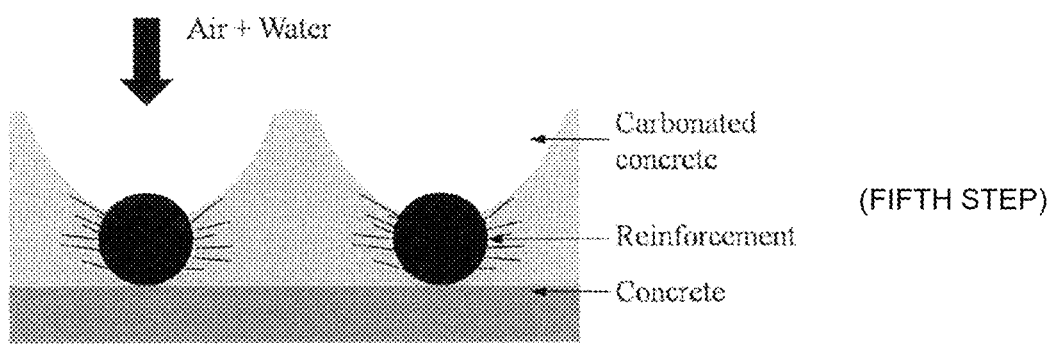
(FIFTH STEP)

[FIG. 8A]
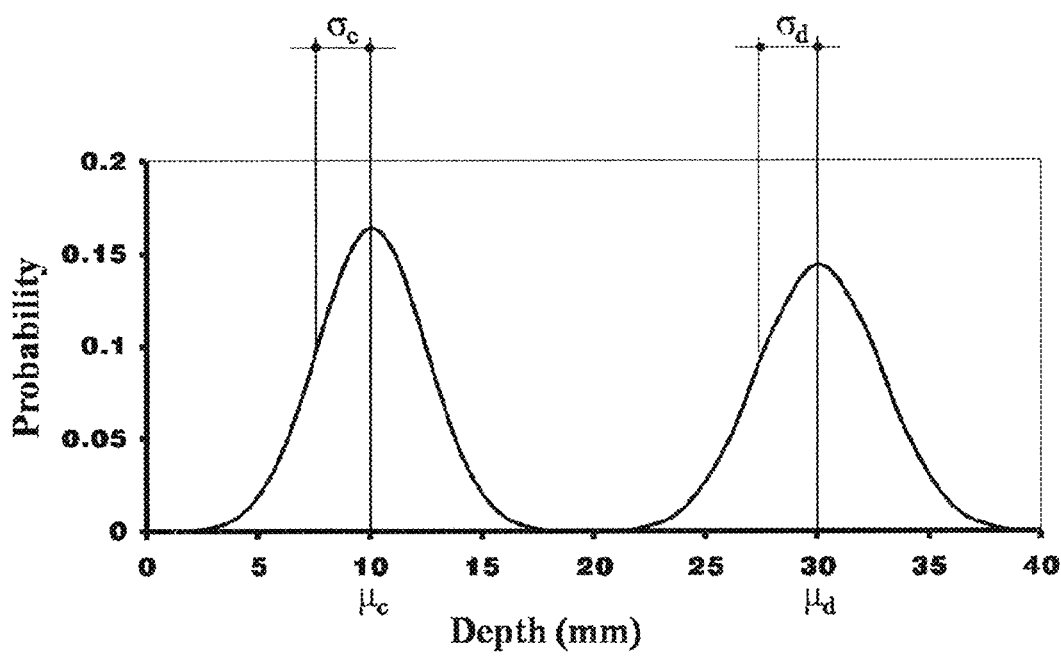
[FIG. 8B]
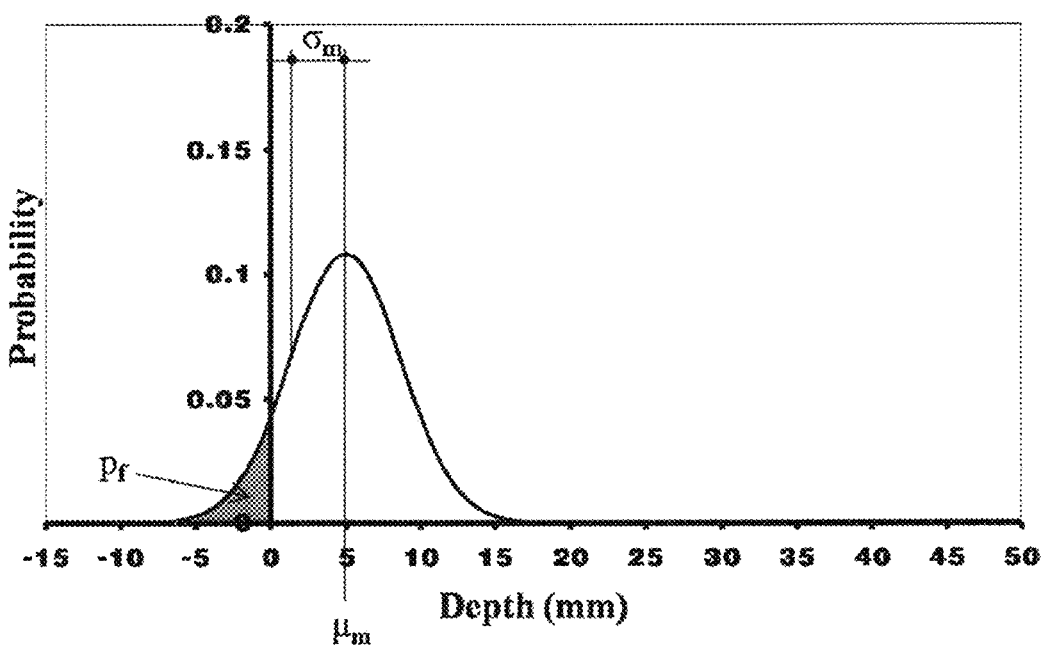

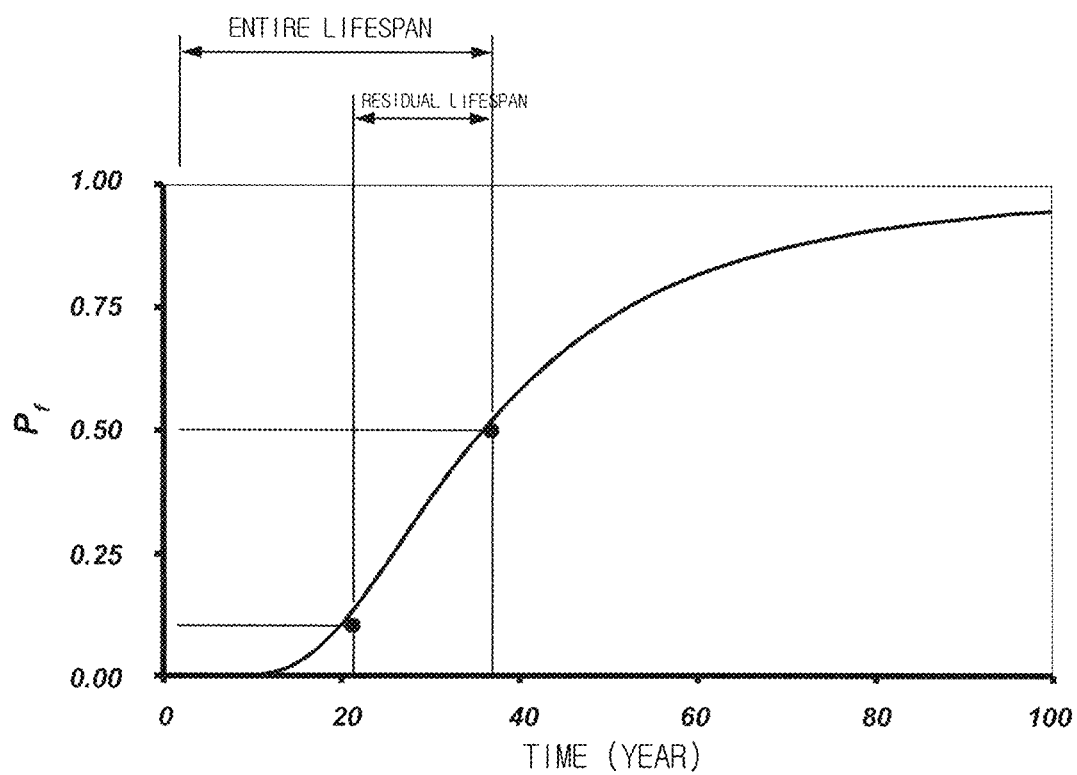
[FIG. 9]

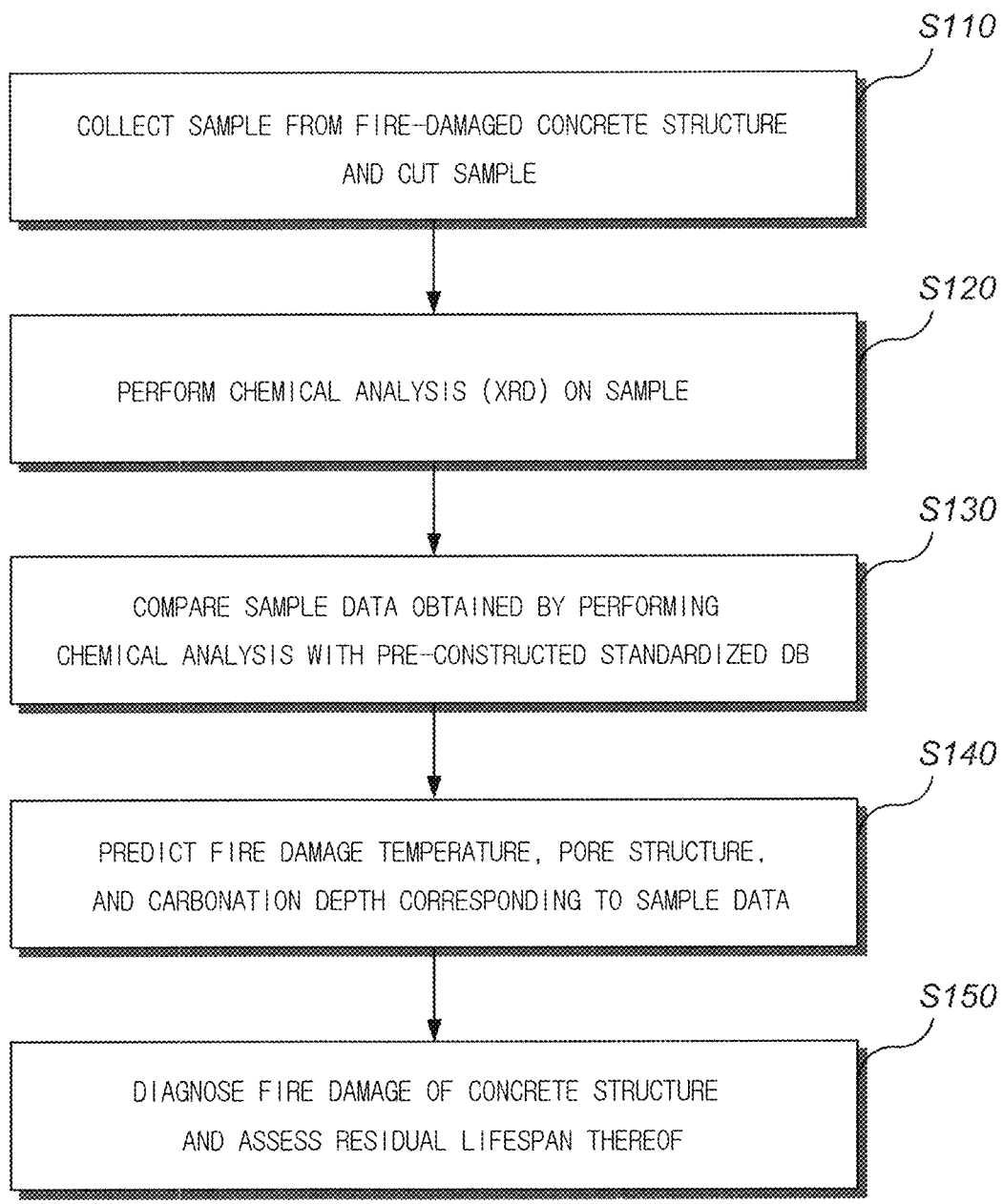
[FIG. 10]

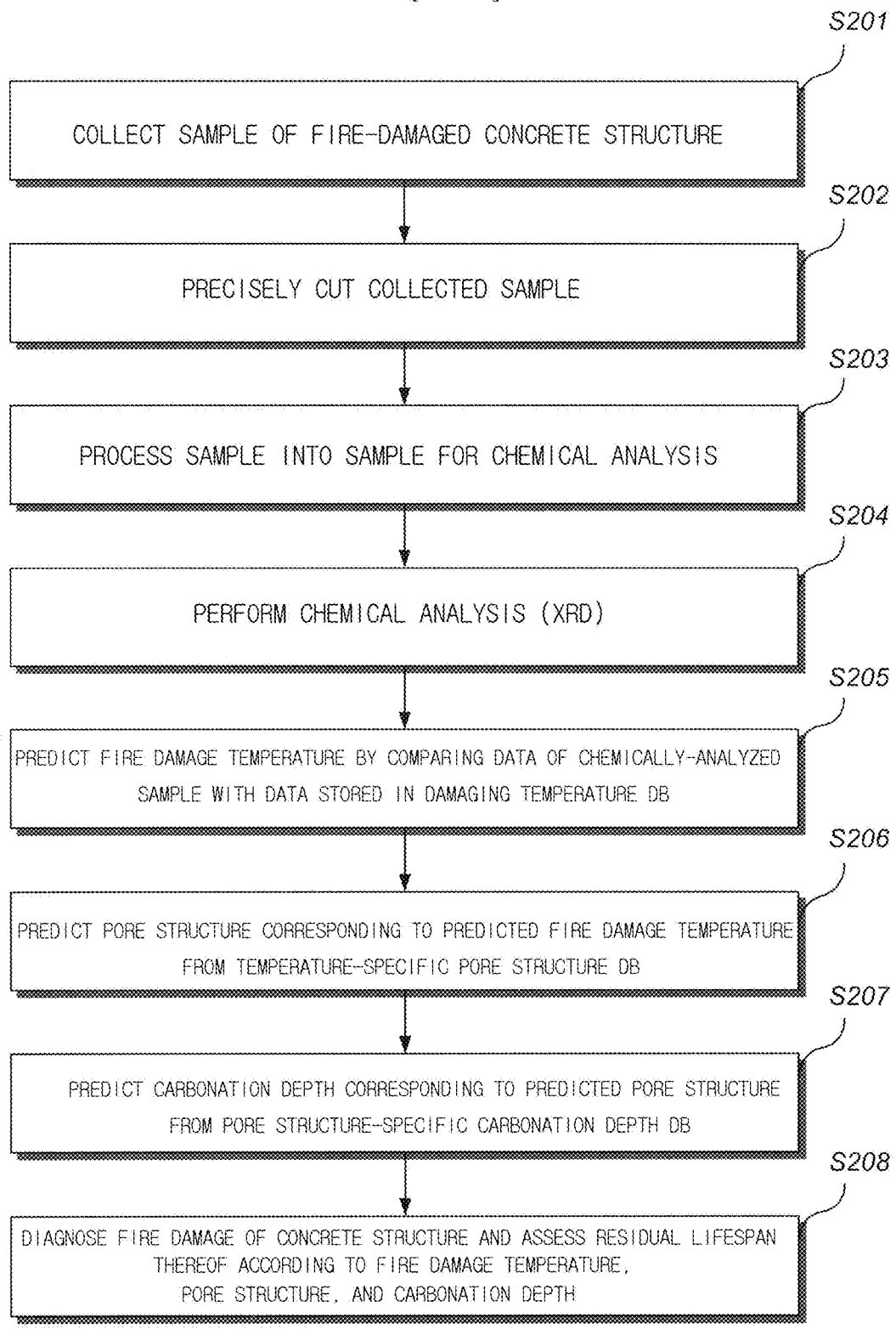
[FIG. 11]

SYSTEM FOR PREDICTING RESIDUAL SERVICE LIFE OF FIRE-DAMAGED CONCRETE STRUCTURES AND METHOD FOR THE SAME

CROSS-REFERENCE TO RELATED APPLICATION

This application is a 371 application of the international PCT application serial no. PCT/KR2015/011402, filed on Oct. 28, 2015, which claims the priority benefit of Korean application no. 10-2014-0184431, filed on Dec. 19, 2014. The entirety of each of the above-mentioned patent applications is hereby incorporated by reference herein and made a part of this specification.

TECHNICAL FIELD

The present invention relates to predicting a residual lifespan of a fire-damaged concrete structure, and more particularly, to a system and a method for collecting a very small amount of a sample from a fire-damaged concrete structure and performing a chemical analysis thereon to predict a residual lifespan of the fire-damaged concrete structure, and predicting the residual lifespan of the fire-damaged concrete structure by performing a comparative analysis of sample data with data pre-stored in a standardized database (DB) constructed through experiments.

BACKGROUND ART

Generally, when a concrete structure is exposed to high temperature, such as in a fire or the like, for a long time, since hardened cement bodies and aggregates show different expansion and shrinkage behaviors, cracks appear or the structure is weakened, and physical properties and fire resistance are noticeably degraded. At this time, a change in pore structure and a chemical change are made, and thermal stress generated by confinement of an end part or the like may cause cracks which causes concrete deterioration and spalling.

Specifically, a hardened cement body has a large amount of chemically-bonded water in addition to free water, and when the hardened body is exposed to 100° C. or higher, free water existing in capillary pores thereof evaporates, and a volume expansion of 1,300 times or more occurs. Also, an internal structure of a paste is loosened, which leads to an increase in pore volume and the development of cracks.

Also, when a heating temperature further rises to about 180° C., a part of the chemically-bonded water begins to evaporate from the hardened cement body. About 20% of the water content of a calcium-silicate hydration product, which is a core hydrate for solidity of the hardened cement body, is lost at a range of about 250° C. to about 350° C., and most of the water content is lost at a range of about 400° C. to 700° C. Within a similar temperature range, calcium hydroxide ($Ca(OH)_2$), which is a free alkali component in concrete, is also pyrolyzed into calcium oxide and water and chemically damaged. Also, since the number of slightly large pores increase and hardness is lost, the hardened cement body becomes structurally very dangerous. Subsequently, when the concrete is heated at about 1200° C. or higher for a long time, the concrete melts from a surface of the structure.

FIG. 1 is a diagram exemplifying compressive strength of a concrete structure being lowered with an increase in temperature during a fire.

As shown in FIG. 1, cement hydrates in concrete of the concrete structure undergo a chemical change in accordance to an increase in heating temperature, and a cement paste and an aggregate show contrary behaviors, that is, shrinkage and expansion, respectively, at temperatures up to about 600° C. Further, as a result of the expansion of free water or the like existing in concrete capillary pores, internal stress gradually increases, and an internal structure is destroyed. Therefore, mechanical properties, such as solidity, elasticity, etc., are degraded. This is mainly because internal destruction resulting from a difference in a thermal expansion coefficient between the cement paste and the aggregate according to quality characteristics has influence on the mechanical properties of the concrete.

Here, the degree of degradation varies according to types, proportions, material ages, etc. of used materials and exhibits a tendency shown in FIG. 1. In other words, solidity is barely degraded up to 300° C., but becomes 50% or less above 500° C. Also, at about 700° C., solidity may be degraded to be in a range of about 60% to 80% of room-temperature compressive strength. Accordingly, it can be seen that compressive strength of concrete is noticeably degraded when the concrete is heated to a high temperature by a fire. Also, it can be seen that an elastic modulus is lowered by heat and is almost halved at 500° C. This is because concrete lose elasticity and gradually becomes plastic when the concrete is heated to a high temperature.

Meanwhile, when a fire occurs, such a concrete structure is degraded in performance due to a change in a microstructure thereof. Such a change in microstructure can be identified from a pore distribution or pore structure characteristics using a gas adsorption method of adsorbing nitrogen onto a concrete structure at nitrogen's boiling point (−195.8° C.) to measure a pore structure thereof.

To determine whether to reuse a fire-damaged concrete structure and a damage level thereof on the basis of a fire mechanism in such a concrete structure, it is necessary to accurately diagnose performance degradation of the concrete structure.

However, up to now, there has been neither an expert nor technology for logically describing the degree of fire damage to a concrete structure in which a fire has occurred. In other words, since there has thus far been no technology for diagnosing a fire-damaged concrete structure, an appropriate assessment is not being made. Accordingly, it is necessary to develop an assessment tool for predicting a residual lifespan of a fire-damaged concrete structure.

PRIOR ART LITERATURE

Patent Literature (Patent Literature 1) Korean Patent No. 10-631485 (date of filing: Mar. 27, 2006), title of invention: "Fast curing coating layer formation method for enhanced durability and preventing neutralization and salt damage of concrete structure and steel structure"

(Patent Literature 2) Korean Patent No. 10-835848 (date of filing: Apr. 19, 2006), title of invention: "Automatic analysis method for the strength of the shotcrete lining under construction and the deteriorated concrete with aging"

(Patent Literature 3) Korean Patent No. 10-894084 (date of filing: Oct. 12, 2007), title of invention: "Distinction method for composition in concrete"

(Patent Literature 4) Korean Patent No. 10-1128455 (date of filing: Aug. 13, 2010), title of invention: "Method for measuring degree of hydration in concrete using backscattered electron imaging"

DISCLOSURE

Technical Problem

To solve the above-described problem, the present invention is directed to providing a system and method for predicting a residual lifespan of a fire-damaged concrete structure which are capable of acquiring sample data by performing a chemical analysis on a sample of a fire-damaged concrete structure, and rapidly predicting a residual lifespan of the fire-damaged concrete structure by comparing the acquired sample data with data pre-stored in a standardized database (DB).

The present invention is directed to providing a system and method for predicting a residual lifespan of a fire-damaged concrete structure which are capable of accurately and scientifically assessing a level of fire damage to a fire-damaged concrete structure so that the fire-damaged concrete structure can be appropriately repaired and reinforced.

Technical Solution

One aspect of the present invention provides a system for predicting a residual lifespan of a fire-damaged concrete structure, the system including: a fire-damaged concrete structure sample collected from a fire-damaged concrete structure and processed into a specimen for chemical analysis; a concrete structure residual lifespan prediction unit configured to diagnose fire damage to the fire-damaged concrete structure by comparing sample data with data pre-stored in a standardized database (DB), and assess a residual lifespan of the fire-damaged concrete structure; and the standardized DB constructed by storing data pre-acquired through an experiment, wherein the standardized DB standardizes and stores experimental data acquired through precise experimentation employing a fire-damaged concrete structure diagnosis device.

Here, for an x-ray diffraction (XRD) analysis, a Brunauer-Emmett-Teller (BET) analysis, and an accelerated carbonation analysis test, the fire-damaged concrete structure diagnosis device may make a total of 20 measurements by making one measurement every time a heating temperature of a concrete structure specimen increases by 50° C., and then store each piece of data to construct the standardized DB.

Here, the fire-damaged concrete structure sample may be collected by drilling into the concrete structure to a target point using a mobile core drill, precisely processed, and then finely ground using an agate mortar set to be processed into the specimen for chemical analysis.

Here, the concrete structure residual lifespan prediction unit may include: a chemical analysis unit configured to acquire the sample data by performing a chemical analysis on the fire-damaged concrete structure sample processed into the specimen for chemical analysis; a data analysis unit configured to separately predict a fire damage temperature, a pore structure, and a carbonation depth by comparing the sample data acquired by the chemical analysis unit with the data pre-stored in the standardized DB; and a fire damage diagnosis and residual lifespan assessment unit configured to diagnose fire damage of the fire-damaged concrete structure sample according to the fire damage temperature, the pore structure, and the carbonation depth analyzed by the data analysis unit and assess the residual lifespan.

Here, the data analysis unit may include: a fire damage temperature prediction unit configured to predict the fire damage temperature by comparing the sample data acquired by the chemical analysis unit with damaging temperature data pre-stored in the standardized DB; a pore structure prediction unit configured to predict temperature-specific pore structures by comparing the sample data acquired by the chemical analysis unit with temperature-specific pore structure data pre-stored in the standardized DB; and a carbonation depth prediction unit configured to predict a carbonation depth by comparing the sample data acquired by the chemical analysis unit with pore structure-specific carbonation depth data pre-stored in the standardized DB.

Here, the standardized DB may include: a damaging temperature DB configured to store real-time chemical property change data in accordance with a fire damage temperature and acquired through an XRD analysis of the fire-damaged concrete structure; a temperature-specific pore structure DB configured to store pore structure characteristic change data in accordance with a fire damage temperature and acquired through a Brunauer-Emmett-Teller (BET) analysis of the fire-damaged concrete structure; and a pore structure-specific carbonation depth DB configured to store carbonation depth data in accordance with a change in pore structure and acquired through a carbonation analysis of the fire-damaged concrete structure.

Another aspect of the present invention provides a method for predicting a residual lifespan of a fire-damaged concrete structure, the method including: a) collecting a sample from a fire-damaged concrete structure and precisely cutting the sample; b) performing a chemical analysis on the precisely cut sample; c) comparing sample data obtained by performing the chemical analysis with data stored in a pre-constructed standardized DB; d) separately predicting a fire damage temperature, a pore structure, and a carbonation depth corresponding to the sample data from the standardized DB; and e) diagnosing fire damage to the fire-damaged concrete structure and assessing a residual lifespan thereof according to the fire damage temperature, the pore structure, and the carbonation depth, wherein the standardized DB standardizes and stores experimental data acquired through precise experimentation employing a fire-damaged concrete structure diagnosis device.

Advantageous Effects

According to the present invention, it is possible to acquire sample data by performing a chemical analysis on a sample of a fire-damaged concrete structure, and rapidly predict a residual lifespan of the fire-damaged concrete structure by comparing the acquired sample data with data pre-stored in a standardized database (DB).

According to the present invention, it is possible to accurately and scientifically assess a level of fire damage to a fire-damaged concrete structure so that the fire-damaged concrete structure can be appropriately repaired and reinforced. Accordingly, a residual lifespan of the fire-damaged concrete structure is predicted, and the concrete structure is managed in consideration of appropriate repair and reinforcement times so that performance of the concrete structure can be improved.

DESCRIPTION OF DRAWINGS

FIG. 1 is a diagram exemplifying compressive strength of a concrete structure being lowered with an increase in temperature during a fire.

FIG. 2 is a diagram showing a configuration of a system for predicting a residual lifespan of a fire-damaged concrete structure according to an exemplary embodiment of the present invention.

FIG. 3 is a diagram exemplifying a standardized database (DB) constructed by a system for predicting a residual lifespan of a fire-damaged concrete structure according to an exemplary embodiment of the present invention.

FIG. 4 is a diagram exemplifying an x-ray diffraction (XRD) analysis device for chemical analysis in a system for predicting a residual lifespan of a fire-damaged concrete structure according to an exemplary embodiment of the present invention.

FIGS. 5A to 5C are diagrams exemplifying XRD analysis results for a concrete structure.

FIG. 6A is a diagram showing a pore distribution of pore size according to a heating temperature, and FIG. 6B is a diagram showing a fine pore ratio according to the heating temperature.

FIGS. 7A-7E are diagrams illustrating performance degradation of concrete caused by carbonation.

FIG. 8A is a diagram showing probability distributions of carbonation depth and cover thickness, and FIG. 8B is a diagram showing a probability distribution of a limit state function.

FIG. 9 is a diagram exemplifying a residual lifespan of a concrete structure in a limit state.

FIG. 10 is an operational flowchart illustrating a method of predicting a residual lifespan of a fire-damaged concrete structure according to an exemplary embodiment of the present invention.

FIG. 11 is a detailed operational flowchart illustrating a method of predicting a residual lifespan of a fire-damaged concrete structure according to an exemplary embodiment of the present invention.

MODES OF THE INVENTION

Hereinafter, exemplary embodiments of the present invention will be described in detail with reference to the accompanying drawings so that those of ordinary skill in the art to which the present invention pertains can implement the present invention. However, the present invention can be embodied in various different forms and is not limited to embodiments described herein. To clearly describe the present invention, parts which are not related to description will be omitted from the drawings, and like parts are denoted by like reference numerals in this specification.

Throughout this specification, when a certain part "includes" a certain component, the description means that another component may be further included and does not exclude another component unless particularly stated otherwise. Further, terms, such as " . . . unit" and the like used in this specification refer to a unit for processing at least one function or operation and may be implemented by hardware, software, or a combination thereof.

[System for Predicting Residual Lifespan of Fire-Damaged Concrete Structure]

FIG. 2 is a diagram showing a configuration of a system for predicting a residual lifespan of a fire-damaged concrete structure according to an exemplary embodiment of the present invention, and FIG. 3 is a diagram exemplifying a standardized database (DB) constructed by a system for predicting a residual lifespan of a fire-damaged concrete structure according to an exemplary embodiment of the present invention.

Referring to FIGS. 2 and 3, a system for predicting a residual lifespan of a fire-damaged concrete structure according to an exemplary embodiment of the present invention generally includes a fire-damaged concrete structure sample 100, a concrete structure residual lifespan prediction unit 200, a standardized DB 300, and a fire-damaged concrete structure diagnosis device 400, and the concrete structure residual lifespan prediction unit 200 includes a chemical analysis unit 210, a data analysis unit 220, and a fire damage diagnosis and residual lifespan assessment unit 230.

The fire-damaged concrete structure sample 100 is collected from a fire-damaged concrete structure by, for example, drilling into the concrete structure to a target point using a mobile core drill, and is precisely processed. Here, the sample 100 may have various sizes, and a preferable size is a diameter of 10 mm×a length of 40 mm. Also, the collected fire-damaged concrete structure sample 100 is precisely cut using a laser cutter or the like. For example, the collected fire-damaged concrete structure sample 100 may be cut into various sizes, and a total of four samples may be prepared according to depths by cutting the fire-damaged concrete structure by 10 mm each time. Each of the four fire-damaged concrete structure samples 100 is finely ground using an agate mortar set or the like to be processed into a specimen for chemical analysis. Here, the agate mortar set refers to a hand mill which is made from agate and used to break a solid mineral specimen in a laboratory.

The concrete structure residual lifespan prediction unit 200 acquires sample data by performing a chemical analysis on the fire-damaged concrete structure samples 100 which have been processed into specimens for chemical analysis, and separately predicts a fire damage temperature, a pore structure, and a carbonation depth by comparing the acquired sample data with data pre-stored in the standardized DB 300 to diagnose fire damage to the fire-damaged concrete structure samples 100 and assess a residual lifespan thereof.

Specifically, the chemical analysis unit 210 of the concrete structure residual lifespan prediction unit 200 performs a chemical analysis on the fire-damaged concrete structure samples 100 which have been processed into the specimens for chemical analysis and acquires sample data.

The data analysis unit 220 of the concrete structure residual lifespan prediction unit 200 compares the sample data acquired by the chemical analysis unit 210 with the data pre-stored in the standardized DB 300 to separately predict a fire damage temperature, a pore structure, and a carbonation depth.

Here, the data analysis unit 220 may include a fire damage temperature prediction unit 221, a pore structure prediction unit 222, and a carbonation depth prediction unit 223. Specifically, the fire damage temperature prediction unit 221 of the data analysis unit 220 compares the sample data acquired by the chemical analysis unit 210 with data pre-stored in a damaging temperature DB 310 of the standardized DB 300 and predicts the fire damage temperature. The pore structure prediction unit 222 of the data analysis unit 220 compares the sample data with data pre-stored in a temperature-specific pore structure DB 320 of the standardized DB 300 and predicts temperature-specific pore structures. The carbonation depth prediction unit 223 of the data analysis unit 220 compares the sample data with data pre-stored in a pore structure-specific carbonation depth DB 330 of the standardized DB 300 and predicts the carbonation depth.

The fire damage diagnosis and residual lifespan assessment unit 230 of the concrete structure residual lifespan prediction unit 200 diagnoses fire damage to the fire-damaged concrete structure samples 100 and assesses a residual lifespan according to the fire damage temperature, the pore structures, and the carbonation depth analyzed by the data analysis unit 220.

The standardized DB 300 standardizes and stores experimental data acquired through precise experimentation employing the fire-damaged concrete structure diagnosis device 400, and the experimental data is used as comparative data for the sample data acquired by the chemical analysis unit 210. Such a data comparison method is similar to, for example, a method of finding an element name using existing data when analyzing an unknown element. The standardized DB 300 according to an exemplary embodiment of the present invention includes the damaging temperature DB 310, the temperature-specific pore structure DB 320, and the pore structure-specific carbonation depth DB 330.

The damaging temperature DB 310 of the standardized DB 300 stores real-time chemical property change data according to a fire damage temperature acquired through a chemical analysis, such as an x-ray diffraction (XRD) analysis or the like, of the fire-damaged concrete structure.

The temperature-specific pore structure DB 320 of the standardized DB 300 stores pore structure characteristic change data according to a fire damage temperature acquired through a pore volume analysis device, such as a Brunauer-Emmett-Teller (BET) analysis or the like, of the fire-damaged concrete structure.

The pore structure-specific carbonation depth DB 330 of the standardized DB 300 stores carbonation depth data according to a change in pore structure acquired through an accelerated carbonation analysis of the fire-damaged concrete structure.

For the XRD analysis, the BET analysis, and the accelerated carbonation analysis, the fire-damaged concrete structure diagnosis device 400 may make a total of 20 measurements by making one measurement every time a heating temperature of a concrete structure specimen increases by 50° C., and then store each piece of data to construct the standardized DB 300. At this time, as a common test condition for the XRD analysis, the BET analysis, and the accelerated carbonation analysis, the specimen is heated from 20° C. to 1000° C., and results are analyzed and stored. Here, an XRD device, a BET device, and an accelerated carbonation test device used to analyze a chemical property change, a pore structure characteristic change, and a carbonation depth change are arbitrary examples of analysis equipment, and the analyses may be performed by other equipment. For example, the chemical property change may be analyzed by inductively coupled plasma, and a pore structure characteristic may be analyzed by porosimetry.

Meanwhile, as shown in FIG. 3, the fire-damaged concrete structure diagnosis device 400 may perform the XRD analysis, the BET analysis, and the accelerated carbonation analysis and store data acquired therefrom in the standardized DB 300, and the standardized DB 300 may be provided in common to a plurality of terminals with which the system for predicting a residual lifespan of a fire-damaged concrete structure according to an exemplary embodiment of the present invention is constructed through a web, a digital card, or the like.

For example, Korean ready-mixed concrete manufacturers produce various types of concrete according to mixing conditions and deliver the produced concrete to sites. The standardized DB 300 may be constructed by analyzing all types of mixing condition-specific ready-mixed concrete commonly used in Korea as described above, and it is possible to provide information for predicting residual lifespans of most fire-damaged Korean building structures through the standardized DB 300. In other words, a first concrete mix residual lifespan prediction unit 200*a* may predict a residual lifespan of a fire-damaged concrete structure with respect to a first concrete mix sample 100*a*, a second concrete mix residual lifespan prediction unit 200*b* may predict a residual lifespan of the fire-damaged concrete structure with respect to a second concrete mix sample 100*b*, and an $N^{th}$ concrete mix residual lifespan prediction unit 200*n* may predict a residual lifespan of the fire-damaged concrete structure with respect to an $N^{th}$ concrete mix sample 100*n*.

Meanwhile, FIG. 4 is a diagram exemplifying an XRD analysis device for chemical analysis in a system for predicting a residual lifespan of a fire-damaged concrete structure according to an exemplary embodiment of the present invention, and FIGS. 5A to 5C are diagrams exemplifying XRD analysis results for a concrete structure.

The system for predicting a residual lifespan of a fire-damaged concrete structure according to an exemplary embodiment of the present invention performs a chemical analysis on a fire-damaged concrete structure using an XRD analysis device as shown in FIG. 4.

Specifically, an XRD analysis is a method of emitting x rays toward a surface of a concrete structure sample and then qualitatively and quantitatively identifying chemical constituents of the specimen by analyzing refraction angles of reflected x rays, and in the method, the concrete structure sample is milled into fine powder and chemically analyzed to identify chemical element symbols representing chemical constituents of the powdered sample. A reaction product analysis based on such XRD is an analysis method for easily identifying reaction products of minerals constituting all materials with no chemical analysis and is performed to estimate physical properties of a concrete structure and determine a reason for an abnormality in the physical properties of the concrete structure.

FIG. 5A is a diagram illustrating main peak indicators of hydration products and reaction products, and FIGS. 5B and 5C show XRD analysis results of a reference specimen of a concrete structure. Here, concrete hydration involves calcium oxide reacting with water to form calcium hydroxide, and Calcium Silicate Hydrate (CSH) gel, Calcium Hydroxide (CH), and Calcium Silicate (CS) are main components of cement. Accordingly, an XRD analysis of concrete makes it possible to quantitatively estimate a change of cement hydrates in the concrete caused by a high temperature and estimate a fire temperature and a duration of the temperature.

Specifically, results of heating a specimen of a ferroconcrete structure having no fire damage, which is a reference specimen, to a range of 100° C. to 1,000° C. in an electric furnace are shown in FIGS. 5B and 5C.

According to analysis results, $Ca(OH)_2$ existed at up to 400° C. However, at 600° C. or above, a CH component mostly disappeared while a CaO component appeared and an amount thereof increased with the increase in temperature. This is because, as a temperature of concrete increases during a fire, calcium hydroxide is decomposed and calcite ($CaCO_3$) is decomposed into CaO.

When a surface portion of the specimen reached 800° C., Ca(OH)$_2$, which is a cement hydration product, and CaCO$_3$, which is calcite, were completely decomposed, and peaks thereof disappeared, whereas a peak of Cao was remarkably formed. It can be seen that Ca(OH)$_2$ was completely decomposed but CaCO$_3$, which is calcite, existed through analysis. On the other hand, Ca(OH)$_2$ was assessed as not being decomposed at all at 400° C. at an inner portion of the specimen.

Therefore, for an XRD analysis test, the above-described fire-damaged concrete structure diagnosis device 400 makes a total of 20 measurements by making one measurement every time the heating temperature of the concrete structure specimen increases by 50° C., and then stores each piece of data to construct the damaging temperature DB 310 of the standardized DB 300. According to an exemplary embodiment of the present invention, a manufactured specimen is milled into fine powder and then subjected to an XRD analysis. In this way, reaction products of concrete are qualitatively analyzed, and how much and into which materials cement hydrates are changed by a high temperature is quantitatively analyzed so that it can be seen how concrete reacts according to temperatures of a fire and what kinds of products are generated.

Meanwhile, according to the BET analysis, a concrete structure sample is inserted into a sample tube, and then nitrogen gas is injected into the sample tube so that the nitrogen gas is adsorbed onto the specimen and desorbed therefrom, and a pore size distribution may be measured in this way. Such a BET analysis is used to measure pores with a relatively small radius.

Specifically, a BET analysis method developed by Brunauer, Emmett, and Teller is typically used to measure a surface area of a porous adsorbate. Such a BET analysis method is a measurement method of identifying a monolayer adsorption point using a sorption isotherm and getting a surface area of a sample from the monolayer adsorption point. Such a BET analysis method is given as Equation 1 below by extending Langmuir's monolayer adsorption theory to a multi-layer adsorption theory using three assumptions, that is, (a) surface energy is uniform, (b) there are no interactions between adsorbed molecules, and (c) all adsorption temperatures of two or more layers are the same.

$$\frac{P}{v(P_0 - P)} = \frac{1}{v_m C} + \frac{C-1}{v_m C} \frac{P}{P_0} \quad \text{[Equation 1]}$$

Here, v denotes an adsorption amount under equilibrium pressure, $v_m$ denotes a monolayer adsorption amount, P denotes an adsorption equilibrium pressure, $P_0$ denotes a saturated vapor pressure, and $P/P_0$ denotes a relative pressure, and here C is given as $$C : e^{(q_1 - q_1)/RT}.$$

Therefore, when the monolayer adsorption amount $v_m$ from a solid surface is known, a specific surface area S may be calculated using molecule-occupied sectional area adsorption (the area of nitrogen is 0.162 nm$^2$) as shown in Equation 2 below.

$$S(m^2/g) = 4.35 v_m (cm^3/g) \quad \text{[Equation 2]}$$

Such nitrogen gas adsorption for measuring a pore structure of a concrete structure is based on a principle that since the relative pressure $P/P_0$ increases when gas is adsorbed onto a solid surface up to the saturated vapor pressure $P_0$, a monolayer further forms a multilayer, and capillary condensation as well as adsorption takes place in pores.

Specifically, before such a gas adsorption measurement is made, a cell in which a concrete structure specimen is inserted is covered with a heating bag and subjected to vacuum drawing for preprocessing, liquid nitrogen is inserted in a dewar, and a small amount of adsorption gas is introduced into the specimen cell in stages. At this time, when the dewar filled with liquid nitrogen is placed on the specimen cell to cool the cell, introduced nitrogen gas is physically adsorbed. As a result, property values of a pore structure determined by such a nitrogen gas adsorption measurement may indicate the specific surface area S, a pore structure, and a pore distribution.

Next, a change in pore structure according to a heating temperature for a concrete structure specimen will be described in detail below.

FIG. 6A is a diagram showing a pore distribution of pore size according to a heating temperature, and shows a distribution of pores having sizes of about 0.001 μm to about 0.1 μm according to an exposure temperature condition of a concrete structure using the aforementioned nitrogen gas adsorption. Here, it can be seen that, with an increase in heating temperature of each specimen, a pore volume of fine pores of 0.01 μm or less is reduced while a pore volume of pores of 0.01 μm or more increases.

With an increase in temperature up to 200° C., free water, gel water, and capillary water in concrete evaporates so that the concrete shrinks, and an internal structure of a paste loosens so that a pore volume of fine pores (of about 0.01 μm or less) increases. However, at about 300° C., a part of C—S—H interlayer water and chemically-bonded water of hydrates disappears. Also, in a range of 400° C. to 700° C., since calcium hydroxide (Ca(OH)$_2$) is decomposed, a dehydration volume increases due to an increase in temperature, and diameters of the fine pores (about 0.01 μm or less) increases so that the pore volume of the fine pores (about 0.01 μm or less) is reduced.

Therefore, an overall tendency indicates that a pore volume is reduced in accordance with an increase in heating temperature within a range of the pore size (about 0.001 μm to about 0.1 μm) measured by the nitrogen gas adsorption.

FIG. 6B is a diagram showing a fine pore ratio according to a water-to-cement (W/C) change and a heating temperature condition, and shows a pore volume of fine pores of 0.1 μm or less which can be measured by nitrogen adsorption. As shown in FIG. 6B, the pores of 0.1 μm or less are very fine pores, and thus do not have a significant influence on an overall pore volume of concrete. However, it is judged that even when the fine pores of 0.1 μm or less are reduced, large pores of 0.1 μm or more are increased, and thus the overall pore volume of the concrete increases with an increase in heating temperature. Accordingly, such a change in pore volume results from a destruction of fine pores and a decomposition of calcium hydroxide caused by an increase in heating temperature and dehydration of the number of capillaries, the number of gels, and the like.

Consequently, according to an exemplary embodiment of the present invention, it is possible to see a heating temperature, that is, a pore size distribution according to a fire damage temperature, and for a BET analysis test, the above-described fire-damaged concrete structure diagnosis device 400 may make a total of 20 measurements by making one measurement every time a heating temperature of a concrete structure specimen increases by 50° C., and then store each piece of data to construct the temperature-specific pore structure DB 320 of the standardized DB 300.

Meanwhile, an accelerated carbonation analysis is a method of inserting a sample into a chamber, introducing highly concentrated carbon dioxide into the chamber to promote a reaction, and then measuring a reaction depth between the introduced carbon dioxide and calcium hydroxide existing in the sample by cutting the sample. Using such a measured value, it is possible to determine a penetration depth of carbon dioxide and predict a durability life of concrete, that is, a residual lifespan of a fire-damaged concrete structure.

Specifically, concrete carbonation is described as follows. Cement, which is a main material of ferroconcrete, is strongly alkaline with a pH of about 13 to about 15, and reinforcement bars existing in concrete are not corroded in a general environment. However, reinforcement bars in a concrete structure may be placed in a corrosive environment, i.e., carbonated by carbon dioxide in the air. In other words, output of carbon monoxide and dioxide is increasing in accordance with the recent growth of cities, and carbonation of major buildings is being accelerated thereby. In particular, a pore volume of concrete is closely related to a penetration rate of carbon dioxide, and thus works as the most crucial factor for determining a residual lifespan of a concrete structure.

Reinforcement bars in concrete are covered with an oxide passivation film in an environment with a pH of 11 or more, and thus are not corroded even when there is oxygen in the concrete. However, when carbonation reaches the reinforcement bars and the pH drops below 11, the reinforcement bars are corroded. Here, a time for carbonation to reach the reinforcement bars is clearly in proportion to a pore volume of the concrete. When there is a high pore volume, a rate of reaching the reinforcement bars increases. Generally, a pore volume increases with an increase in W/C. However, a pore volume increases exponentially when concrete is put in a special situation, such as a fire, and a durability life of concrete is shortened due to carbonation.

FIGS. 7A-7B are diagrams illustrating performance degradation of concrete caused by carbonation. As shown in FIG. 7A, in a first carbonation step, there is almost no change in materials and strength and there are only small cracks caused by drying shrinkage. As shown in FIG. 7B, in a second carbonation step, inflation pressure is generated in concrete due to rust generation and cracks are generated. As shown in FIG. 7C, in a third carbonation step, cement above reinforcement bars begin to expand and cracks extend to a surface of the concrete. Therefore, air and water penetration becomes severe and causes other deterioration, such as freezing damage and the like, and it is possible to see rusty water. As shown in FIG. 7D, in a fourth carbonation step, a coating of the cement above the reinforcement bars is broken, the reinforcement bars begin to be exposed, and a sectional area is reduced. Finally, as shown in FIG. 7E, in a fifth carbonation step, most of the cement above the reinforcement bars disappears and the reinforcement bars are exposed to the air and lose durability.

Such concrete carbonation begins with an outer portion of concrete exposed to carbon dioxide and gradually proceeds. However, carbon dioxide should be diffused through pores included in a concrete surface which has already been carbonated, and thus a carbonation rate is gradually reduced. Here, in an environment with uniform humidity, a carbonation depth increases in proportion to the square root of time. This is related to an interaction between carbon dioxide and a pore system, and a carbonation depth C can be expressed as shown in Equation 3 below.

$$C = A\sqrt{t} \qquad \text{[Equation 3]}$$

The concrete carbonation rate is in proportion to the square root of time or in a like form. When the carbonation depth is C and a cover thickness is D, a safety margin of the cover thickness with respect to carbonation can be defined as M=D−C. Assuming that a time for the carbonation depth C to reach reinforcement bars is a lifespan with respect to carbonation, the safety margin denotes a limit state with respect to carbonation in which M is a limit. Therefore, a time for a carbonation depth of a concrete structure to reach reinforcement bars thereof may be a durability life of the structure with respect to carbonation, and it is possible to obtain a residual lifespan of the structure by excluding a measurement time. A limit state function can be expressed by Equation 4.

[Equation 4]

$$M(x,t) = D(x,t) - C(x,t) \qquad \text{[Equation 4]}$$

Here, $M(x, t)$ denotes a limit state with respect to carbonation, $D(x, t)$ denotes a carbonation depth, and $C(x, t)$ denotes a cover thickness.

Also, since carbonation depth data obtained through precise safety diagnosis of a concrete structure may be considered to be a probability distribution of each section, it is possible to calculate probabilistic characteristic values, such as an average, a standard deviation, etc., of each of the sections by analyzing measured section-specific carbonation depth data. In the same way, since a distribution cover thickness value may also be considered to be a random variable in the same section due to errors in design and construction, it is possible to calculate an average and a standard deviation by analyzing measured cover thickness data.

FIG. 8A is a diagram showing probability distributions of the carbonation depth C and the cover thickness D, and FIG. 8B is a diagram showing a probability distribution of a limit state function M with respect to carbonation. Here, each curve denotes a probability density function.

Specifically, assuming that an average and a standard deviation of the carbonation depth C are respectively $\mu_c$ and $\sigma_c$, an average and a standard deviation of the cover thickness D are respectively $\mu_d$ and $\sigma_d$, and distributions of the carbonation depth and the cover thickness are normal distributions, the limit state function M with respect to carbonation also becomes a normal distribution. Here, an average and a standard deviation of the limit state function are respectively given by Equations 5 and 6 below.

$$\mu_m = \mu_d - \mu_c \qquad \text{[Equation 5]}$$

$$\sigma_m = \sqrt{\sigma_d^2 + \sigma_c^2} \qquad \text{[Equation 6]}$$

As shown in FIG. 8B, a cumulative distribution function of 0 or less, that is, $P_f$, can be referred to as a probability that a carbonation depth increases to a cover thickness and reaches reinforcement bars.

Here, $P_f$ is a value calculated by probabilistically approaching a distribution of a cover thickness as well as a carbonation depth, or a progress tendency of carbonation. Therefore, a total lifespan and a residual lifespan of a structure based on such a residual lifespan assessment model are obtained through statistical inference.

FIG. 9 is a diagram exemplifying a residual lifespan of a concrete structure in a limit state, and a limit of $P_f$ may have a range of 0 to 1. For example, to obtain a conservative assessment value, a time for $P_f$ to become 0.5 may be a residual lifespan of a concrete structure as shown in FIG. 9.

Therefore, for an accelerated carbonation analysis test, the above-described fire-damaged concrete structure diagnosis device 400 makes a total of 20 measurements by making one measurement every time a heating temperature of a concrete structure specimen increases by 50° C., and then stores each piece of data to construct the pore structure-specific carbonation depth DB 330 of the standardized DB 300.

According to an exemplary embodiment of the present invention, it is possible to acquire sample data by performing a chemical analysis on a sample of a fire-damaged concrete structure, and to rapidly predict a residual lifespan of the fire-damaged concrete structure by comparing the acquired sample data with data pre-stored in a standardized DB.

According to an exemplary embodiment of the present invention, since it is possible to accurately and scientifically assess a level of fire damage, appropriate repair and reinforcement can be made. In other words, it is possible to improve performance of a fire-damaged concrete structure by predicting a residual lifespan of the concrete structure and managing the concrete structure by considering of appropriate repair and reinforcement times.

[Method of Predicting Residual Lifespan of Fire-Damaged Concrete Structure]

FIG. 10 is an operational flowchart illustrating a method of predicting a residual lifespan of a fire-damaged concrete structure according to an exemplary embodiment of the present invention.

Referring to FIG. 10, the method of predicting a residual lifespan of a fire-damaged concrete structure according to an exemplary embodiment of the present invention first involves collecting the sample 100 from a fire-damaged concrete structure and precisely cutting the sample 100 (S110). Here, the sample 100 is collected by drilling into the concrete structure to a target point using a mobile core drill, is precisely processed, and then is finely ground using an agate mortar set to be processed into a specimen for chemical analysis.

Next, a chemical (XRD) analysis is performed on the precisely cut sample 100 (S120). Subsequently, data of the chemical analysis is used as initial input data.

Next, the sample data on which the chemical analysis is performed is compared with the pre-constructed standardized DB 300 (S130). Here, the standardized DB 300 standardizes experimental data acquired through precise experimentation employing the fire-damaged concrete structure diagnosis device 400 and stores the standardized experimental data. For XRD analysis, BET analysis, or carbonation analysis, the fire-damaged concrete structure diagnosis device 400 makes a total of 20 measurements by making one measurement every time a heating temperature of the concrete structure specimen increases by 50° C., and then stores each piece of data to construct the standardized DB 300.

Next, a fire damage temperature, a pore structure, and a carbonation depth corresponding to the sample data are predicted (S140).

Next, fire damage to the concrete structure is diagnosed and a residual lifespan thereof is assessed (S150).

FIG. 11 is a detailed operational flowchart illustrating a method of predicting a residual lifespan of a fire-damaged concrete structure according to an exemplary embodiment of the present invention.

Referring to FIG. 11, the method of predicting a residual lifespan of a fire-damaged concrete structure according to an exemplary embodiment of the present invention first involves collecting the sample 100 from a fire-damaged concrete structure (S201). Specifically, a sample of the fire-damaged concrete structure is collected in an inward direction from a surface thereof. For example, the concrete structure is drilled to a target point using a mobile core drill. Here, the sample 100 may have various sizes, and a preferable size is a diameter of 10 mm×a length of 40 mm.

Next, the collected sample 100 is precisely cut using a laser cutter or the like (S202). For example, the collected sample 100 may be cut in various sizes, and a total of four samples may be prepared according to depths by cutting the fire-damaged concrete structure by 10 mm each time.

Next, the four samples 100 are processed into samples for chemical analysis (S203). Specifically, each of the four samples 100 is processed into a specimen for chemical analysis. At this time, each of the four samples 100 is finely ground using an agate mortar set or the like. Here, the agate mortar set refers to a hand mill which is made from agate and used to break a solid mineral specimen in a laboratory.

Next, a chemical analysis, for example, XRD, is performed on the specimens for chemical analysis (S204).

Next, data of the chemically-analyzed samples 100 is compared with data stored in the damaging temperature DB 310 in the standardized DB 300 to predict fire damage temperatures thereof (S205). In other words, the data of the chemically-analyzed samples 100 and the data stored in the damaging temperature DB 310 are compared to find temperatures in data of the chemically-analyzed samples 100 which coincide with the data obtained from the damaging temperature DB 310 so that fire damage temperatures of the samples 100 is predicted.

Next, pore structures corresponding to the predicted fire damage temperatures are predicted from the temperature-specific pore structure DB 320 in the standardized DB 300 (S206). In other words, pore structures at the predicted fire damage temperatures which coincide with data obtained from the temperature-specific pore structure DB 320 are found to predict pore structures of the samples 100.

Next, carbonation depths corresponding to the predicted pore structures are predicted from the pore structure-specific carbonation depth DB 330 in the standardized DB 300 (S207). In other words, carbonation depths of the predicted pore structures which coincide with data obtained from the pore structure-specific carbonation depth DB 330 are found.

Next, according to the fire damage temperatures, the pore structures, and the carbonation depths of the samples 100, fire damage to the concrete structure is diagnosed and a residual lifespan thereof is assessed (S208). Since those of ordinary skill in the art should appreciate that it is possible to diagnose the fire damage and assess the residual lifespan according to a change in chemical components, a change in pore structures, and a progress of carbonation, a detailed description thereof will be omitted.

Accordingly, each of the damaging temperature DB 310, the temperature-specific pore structure DB 320, and the pore structure-specific carbonation depth DB 330 in the standardized DB 300 can easily manage information on a change in chemical components, a change in pore structures, and a progress of carbonation according to a change in a temperature of a fire-damaged concrete structure. In other words, using data matching analysis, it is possible to extract data which coincides with data measured through external experimentation and rapidly predict a fire damage temperature, a change in pore volume, and a change in residual lifespan of a fire-damaged concrete structure.

The above descriptions of the present invention are exemplary, and those of ordinary skill in the art to which the present invention pertains should understand that various modifications can be made without departing from the technical spirit or essential characteristics of the present invention. Therefore, it should be understood that the embodiments described above are exemplary in all aspects and are not restrictive. For example, each component which is described in a single form may be implemented in a distributed manner, and similarly, components which are described as being distributed may be implemented in a combined form.

The scope of the present invention is represented by the claims to be described below rather than the detailed descriptions, and the meaning and the scope of the claims and all changed or modified forms derived from the equivalent concept thereof should be interpreted as being included in the scope of the present invention.

The invention claimed is:

1. A system for predicting a residual lifespan of a fire-damaged concrete structure, the system comprising:
    a fire-damaged concrete structure sample (100) collected from a fire-damaged concrete structure and processed into a specimen for chemical analysis;
    a concrete structure residual lifespan prediction unit (200) configured to obtain sample data by performing a chemical analysis on the fire-damaged concrete structure sample (100) processed into the specimen for chemical analysis, separately predict a fire damage temperature, a pore structure, and a carbonation depth of the fire-damaged concrete structure by comparing the sample data with data pre-stored in a standardized database (DB) (300), diagnose fire damage to the fire-damaged concrete structure according to the fire damage temperature, the pore structure, and the carbonation depth, and assess a residual lifespan of the fire-damaged concrete structure according to the diagnosed fire damage; and
    the standardized DB (300) constructed by storing data acquired through experimentation to be compared with the sample data of the chemical analysis performed by the concrete structure residual lifespan prediction unit (200),
    wherein the standardized DB (300) standardizes and stores experimental data acquired through precise experimentation employing a fire-damaged concrete structure diagnosis device (400).

2. The system of claim 1, wherein, for an x-ray diffraction (XRD) analysis, a Brunauer-Emmett-Teller (BET) analysis, and an accelerated carbonation analysis test, the fire-damaged concrete structure diagnosis device (400) makes a total of 20 measurements by making one measurement every time a heating temperature of a concrete structure specimen increases by 50° C., and then stores each piece of data to construct the standardized DB (300).

3. The system of claim 1, wherein the fire-damaged concrete structure sample (100) is collected by drilling into the concrete structure to a target point using a mobile core drill, is precisely processed, and is then finely ground using an agate mortar set to be processed into the specimen for chemical analysis.

4. The system of claim 1, wherein the concrete structure residual lifespan prediction unit (200) comprises:
    a chemical analysis unit (210) configured to acquire the sample data by performing the chemical analysis on the fire-damaged concrete structure sample (100) processed into the specimen for chemical analysis;
    a data analysis unit (220) configured to separately predict the fire damage temperature, the pore structure, and the carbonation depth by comparing the sample data acquired by the chemical analysis unit (210) with the data pre-stored in the standardized DB (300); and
    a fire damage diagnosis and residual-lifespan assessment unit (230) configured to diagnose fire damage of the fire-damaged concrete structure sample (100) according to the fire damage temperature, the pore structure, and the carbonation depth analyzed by the data analysis unit (220) and assess the residual lifespan thereof.

5. The system of claim 4, wherein the data analysis unit (220) comprises:
    a fire damage temperature prediction unit (221) configured to predict the fire damage temperature by comparing the sample data acquired by the chemical analysis unit (210) with damaging temperature data pre-stored in the standardized DB (300);
    a pore structure prediction unit (222) configured to predict temperature-specific pore structures by comparing the sample data acquired by the chemical analysis unit (210) with temperature-specific pore structure data pre-stored in the standardized DB (300); and
    a carbonation depth prediction unit (223) configured to identify a change in durability by comparing the sample data acquired by the chemical analysis unit (210) with pore structure-specific carbonation depth data pre-stored in the standardized DB (300).

6. The system of claim 1, wherein the standardized DB (300) comprises:
    a damaging temperature DB (310) configured to store real-time chemical property change data in accordance with a fire damage temperature and acquired through an x-ray diffraction (XRD) analysis of the fire-damaged concrete structure;
    a temperature-specific pore structure DB (320) configured to store pore structure characteristic change data in accordance with a fire damage temperature and acquired through a Brunauer-Emmett-Teller (BET) analysis of the fire-damaged concrete structure; and
    a pore structure-specific carbonation depth DB (330) configured to store carbonation depth data in accordance with a change in pore structure and acquired through a carbonation analysis of the fire-damaged concrete structure.

7. A method of predicting a residual lifespan of a fire-damaged concrete structure, the method comprising:
    a) collecting a sample (100) from a fire-damaged concrete structure and precisely cutting the sample (100);
    b) performing a chemical (x-ray diffraction (XRD)) analysis on the precisely cut sample (100);
    c) comparing sample data obtained by performing the chemical analysis with data stored in a pre-constructed standardized database (DB) (300);
    d) separately predicting a fire damage temperature, a pore structure, and a carbonation depth corresponding to the sample data from the standardized DB (300); and
    e) diagnosing fire damage to the fire-damaged concrete structure and assessing a residual lifespan thereof according to the fire damage temperature, the pore structure, and the carbonation depth,
    wherein the standardized DB (300) standardizes and stores experimental data acquired through precise experimentation employing a fire-damaged concrete structure diagnosis device (400).

8. The method of claim 7, wherein, for the XRD analysis, a Brunauer-Emmett-Teller (BET) analysis, and an accelerated carbonation analysis test, the fire-damaged concrete structure diagnosis device (400) makes a total of 20 measurements by making one measurement every time a heating temperature of a concrete structure specimen increases by 50° C., and then stores each piece of data to construct the standardized DB (300).

9. The method of claim 7, wherein the sample (100) of step a) is collected by drilling into the concrete structure to a target point using a mobile core drill, is precisely processed, and then is finely ground using an agate mortar set to be processed into a specimen for chemical analysis.

10. The method of claim 7, wherein the standardized DB (300) of step c) comprises:
- a damaging temperature DB (310) configured to store real-time chemical property change data in accordance with a fire damage temperature and acquired through an XRD analysis of the fire-damaged concrete structure;
- a temperature-specific pore structure DB (320) configured to store pore structure characteristic change data in accordance with a fire damage temperature and acquired through a Brunauer-Emmett-Teller (BET) analysis of the fire-damaged concrete structure; and
- a pore structure-specific carbonation depth DB (330) configured to store carbonation depth data in accordance with a change in pore structure and acquired through a carbonation analysis of the fire-damaged concrete structure.

* * * * *